US012491515B2

(12) United States Patent
Asghar

(10) Patent No.: US 12,491,515 B2
(45) Date of Patent: Dec. 9, 2025

(54) SYSTEMS AND METHODS FOR SPERM SELECTION

(71) Applicant: Florida Atlantic University Research Corporation, Boca Raton, FL (US)

(72) Inventor: Waseem Asghar, Boca Raton, FL (US)

(73) Assignee: Florida Atlantic University Research Corporation, Boca Raton, FL (US)

( * ) Notice: Subject to any disclaimer, the term of this patent is extended or adjusted under 35 U.S.C. 154(b) by 1256 days.

(21) Appl. No.: 17/269,837

(22) PCT Filed: Aug. 20, 2019

(86) PCT No.: PCT/US2019/047254

§ 371 (c)(1),
(2) Date: Feb. 19, 2021

(87) PCT Pub. No.: WO2020/041303

PCT Pub. Date: Feb. 27, 2020

(65) Prior Publication Data

US 2021/0178394 A1 Jun. 17, 2021

Related U.S. Application Data

(60) Provisional application No. 62/720,601, filed on Aug. 21, 2018.

(51) Int. Cl.
*B01L 3/00* (2006.01)
*C12N 5/071* (2010.01)

(52) U.S. Cl.
CPC ...... *B01L 3/502761* (2013.01); *C12N 5/0612* (2013.01); *B01L 2200/0652* (2013.01); (Continued)

(58) Field of Classification Search
CPC .................. C12N 5/0612; C12M 47/04; B01L 2200/0652
See application file for complete search history.

(56) References Cited

U.S. PATENT DOCUMENTS

2011/0114869 A1 5/2011 Schaeffer et al.
2014/0273192 A1 9/2014 Sharpe et al.
(Continued)

OTHER PUBLICATIONS

International Search Report issued in PCT/US2019/047254 on Nov. 7, 2019.

*Primary Examiner* — Maris R Kessel
*Assistant Examiner* — Mickey Huang
(74) *Attorney, Agent, or Firm* — Fox Rothschild LLP

(57) ABSTRACT

Systems for sorting sperm include a housing and a microfluidic system supported by the housing. The systems also include two or more inlets providing access to the microfluidic system to deliver sperm or semen and fluid to the microfluidic system, as well as an outlet for harvesting sorted sperm. The systems include a flow channel that provides a flow path for sperm from an inlet to an outlet while sperm travels against a fluid flow towards an outlet for harvesting. In the systems, fluid delivered to the microfluidic system via an inlet flows from the inlet towards one or more outlets, and the flow channel extending along the length of the microfluidic system provides a flow path for motile sperm to travel against the fluid flow towards a collection outlet for harvesting. In some embodiments of a system, the microfluidic system also includes a microporous filter arranged in the flow path between the inlet and the collection outlet to cause motile sperm traveling against the fluid flow to pass through the filter to reach the collection outlet for harvesting.

18 Claims, 12 Drawing Sheets

(52) U.S. Cl.
CPC .................. *B01L 2300/0816* (2013.01); *B01L 2300/0832* (2013.01); *B01L 2300/123* (2013.01)

(56) References Cited

U.S. PATENT DOCUMENTS

| | | | |
|---|---|---|---|
| 2014/0315281 | A1 | 10/2014 | Pan |
| 2016/0290913 | A1 | 10/2016 | Demirci et al. |
| 2018/0119087 | A1 | 5/2018 | Chin et al. |

c

SYSTEMS AND METHODS FOR SPERM SELECTION

CROSS-REFERENCE TO RELATED APPLICATIONS

This application is a National Phase Entry of PCT/US2019/047254 filed on Aug. 20, 2019, entitled "SYSTEMS AND METHODS FOR SPERM SELECTION", which claims priority to U.S. Provisional Patent Application No. 62/720,601 filed on Aug. 21, 2018, both of which are incorporated herein by reference in their entireties.

FIELD OF THE INVENTION

The invention relates generally to the fields of microfluidics and medicine. In particular, the invention relates to systems and methods for sorting healthy motile sperm from less motile sperm.

BACKGROUND

Infertility affects roughly 48.5 million couples worldwide and 30-50% of these cases are caused by male factor infertility. Assisted reproductive technologies (ART), such as intracytoplasmic sperm injection (ICSI), intrauterine insemination (IUI) and in vitro fertilization (IVF) offer infertile couples the opportunity to start families. However, only about a third of ART cycles result in a birth. Sperm processing is an important part of the ART cycle and there are several factors to consider when determining the quality of sperm, such as sperm concentration, motility, morphology, DNA integrity and levels of reactive oxygen species (ROS). Infertile men tend to have abnormal sperm parameters, such as low concentration, abnormal morphology and elevated levels of DNA damage and ROS.

The most frequently used methods of sperm sorting and processing including sperm washing, direct swim-up (DSW) and discontinuous density gradient centrifugation (DGC) involve multiple centrifugation steps that are damaging to sperm cells (Rappa et al., Biotechnology Advances 34, 578-587 (2016); Asghar et al., Advanced Healthcare Materials (2014); Nosrati et al., Lab on a Chip 14, 1142-1150 (2014)). Centrifugation creates a sperm pellet that can also include inflammatory cells and immature sperm, which produce ROS and can cause DNA fragmentation in the healthy sperm cells. In natural reproduction, a successful pregnancy occurs when sperm travel through the female genital tract and fertilize the oocyte in the oviduct. Only about one sperm per every million sperm ejaculated makes it to the oviduct. The small amount of sperm that are capable of fertilizing the oocyte indicates that natural sperm selection has a stringent sperm selection process that incorporates muscular contractions and significant fluid flow against the sperm swimming direction. Rheotaxis, a phenomenon where sperm cells swim against the flow direction is possibly the long-range sperm guidance mechanism for successful fertilization. Centrifugation is not involved in natural sperm selection in the female genital track, hence current lab-based sperm sorting methods produce unknown bias and damage sperm cells. Hence, it is important to continue to search for ways to improve sperm processing and sorting procedures to create the best pregnancy outcomes.

Microfluidics has emerged as an alternative technology with precise control to sort and isolate cells within small volumes. Microfluidics has been widely investigated for various applications in cell sorting, disease diagnostics and regenerative medicine (Asghar et al., Biotechnology Journal 9, 895-903 (2014); Kanakasabapathy et al., Lab on a Chip 17, 2910-2919 (2017); Coarsey et al., Critical Reviews in Microbiology 43, 779-798 (2017)). More recently, microfluidic-based devices have been reported to sort and select healthy sperm to be utilized in ART procedures (Knowlton et al., Trends in Biotechnology 33, 221-229 (2015); Rappa et al., Biotechnology Advances 34, 578-587 (2016)). Microfluidic technology provides precise control to optimize the microchannel dimensions and surface topography such that motile sperm cells are enriched after sorting (Tung et al., Lab on a Chip 14, 1348-1356 (2014); Chinnasamy et al., Advanced Science 5, 1700531 (2018)). Using microfluidic technology, sperm are either sorted based on their passive motility or microfluidic based sorting is integrated with sperm guidance mechanisms such as chemotaxis and thermotaxis (Knowlton et al., Trends in Biotechnology 33, 221-229 (2015); Rappa et al., Biotechnology Advances 34, 578-587 (2016)). More recently, flow-driven microfluidic devices have also been developed (Cho et al., Anal Chem 75, 1671-1675 (2003); Seo et al., Microfluidics and Nanofluidics 3, 561-570 (2007); Chen et al., Analyst 138, 4967-4974 (2013)) where motile sperm cells either flow with or against the flow during the sorting process, however these microfluidic devices are not utilized in clinical practice and require further investigation. It is unclear in the literature whether microfluidic-based sperm sorting provides any quantifiable advantage over other technologies in terms of sperm functional parameters including sperm velocity. What is needed is a sperm processing technique that is able to select normal sperm mimicking natural sperm selection, while eliminating damaging centrifugation steps and harmful substances such as dead cells and ROS-producing leukocytes that can cause damage.

SUMMARY

Described herein are systems and methods for (i) development of a chemical-free and centrifugation-free system to sort healthy sperm with high motility, (ii) isolation of the sorted healthy sperm, and (iii) developing a better understanding of sperm rheotaxis. This platform is an innovation beyond the existing clinical procedures such as the Swim-up and microdrop techniques. It is also novel beyond the reported microfluidic-based sperm sorting devices, as it uses a new ground-breaking knowledge of rheotaxis in microfluidic channels for sorting sperm. Given that clinical reproductive medicine has been a challenging field that is labor intensive, such an easy-to-use microchip (microfluidic system) can lead to improved selection of healthy sperm and decreased dependence on operator skills, facilitating repeatable and reliable operational steps. The systems and methods described herein overcome the drawbacks of known sorting systems by providing a system and method that integrates sperm's natural aptitude to swim against the flow through micro- and macro-fluidics to sort sperm in a manner that allows efficient selection of sperm that are favorably suited to fertilization. In particular, sperm suited to fertilization are most desirable and can be selected or sorted using a system that presents an environment that is akin to that presented in the fertilization process. In the systems and methods described herein, inlets and outlets are connected by microfluidic channels to approximate the female genital track. Fluid is flown from an inlet to a collection outlet and sperm that are motile travel against the fluid flow due to rheotaxis. The dead, less functional sperm and semen plasma cannot travel against the flow direction, hence only motile, healthy and functional sperm can make it to the collection outlet. Further, sperm are washed from semen plasma during the sorting process.

Accordingly, described herein is a system for sorting sperm including: a flexible housing operably connected to a substrate having a first end and a second end; a microfluidic system supported by the flexible housing; a first inlet positioned proximate to the first end and providing access to the microfluidic system to deliver fluid to the microfluidic system; a second inlet disposed distal to the first end and providing access to the microfluidic system to deliver sperm to the microfluidic system; an outlet including a collection chamber providing access to the microfluidic system to collect sorted sperm from the microfluidic system, the outlet disposed between the first inlet and the second inlet; a waste chamber providing access to the microfluidic system for collecting waste fluid from the microfluidic system, the waste chamber disposed proximate to the second end; and a flow channel extending from the first inlet to the waste chamber that provides a flow path for sperm to travel from the second inlet to the collection chamber against a fluid flow from the first inlet to the waste chamber. In the system, the first inlet, the second inlet, the outlet, and the waste chamber are fluidly connected to the flow channel and the flow channel is about 1 mm to about 50 mm in length, about 1 mm to about 20 mm in width, and about 25 μm to about 250 μm in height. The microfluidic system is configured such that fluid flows between the first inlet and the outlet, and between the outlet and the second inlet, at a speed higher than fluid flows along all other points of the flow channel. In the system, the first inlet is generally cylindrical and about 0.5 mm to about 1.5 mm in diameter and about 1.5 mm to about 3 mm in height. In the system, the second inlet is generally cylindrical and about 3 mm to about 20 mm in diameter and about 1.5 mm to about 3 mm in height. In the system, the outlet has dimensions of about 5 mm-11 mm×2.5 mm elliptical and about 1.5 mm to about 3 mm in height. In some embodiments of the system, the substrate is a glass slide. In the system, the housing can include Polydimethylsiloxane (PDMS), poly-(methyl methacrylate) (PMMA), a flexible plastic, or combination thereof. In a typical embodiment, the outlet is elliptical and the waste chamber is cylindrical. The system can further include a syringe, a syringe pump, and tubing operably and fluidly connected to the first inlet. The system (for example, when in use) can further include sperm and a fluid including a sperm preparation buffer. The system can further include an imaging system for imaging the sperm within the flow path and/or collection chamber and/or a heating system to maintain a temperature of 37° C.

Also described herein is a method for sorting sperm. The method includes: providing a system for sorting sperm according to the embodiments described in the paragraph above; delivering a suitable amount of fluid to the first inlet of the system such that the microfluidic system is substantially filled with fluid; continuing to deliver fluid and increasing the fluid's flow rate to 10 μl/minute or greater such that the fluid flows from the first inlet to the waste chamber resulting in a flow path, and fluid flows between the first inlet and the outlet, and between the outlet and the second inlet, at a speed higher than fluid flows along all other points of the flow channel; delivering a sample including sperm to the second inlet of the system, wherein the flow speed of 10 μl/minute or greater prevents sperm delivered to the second inlet from entering the collection chamber; lowering the flow speed to a speed of about 0.5 μl/minute to about 8 μl/minute for a suitable period of time such that motile sperm travel against the fluid flow and enter the collection chamber; and harvesting motile sperm that have entered the collection chamber. In the method, harvesting motile sperm that have entered the collection chamber can include compressing (e.g., pinching) at least a portion of the flexible housing adjacent to sides of the collection chamber while harvesting the sperm. In the method, delivering a suitable amount of fluid to the first inlet can include flowing fluid through a syringe, a syringe pump, and tubing that is operably and fluidly connected to the first inlet. The method can further include imaging the sperm as they travel against the fluid flow and enter the collection chamber. The method can further include heating the system to maintain a temperature of 37° C.

Further described herein is a system for sorting sperm that includes: a housing operably connected to a substrate (e.g., a glass slide) having a first end and a second end; a microfluidic system supported by the housing; at least a first semen inlet positioned proximate to the first end and providing access to the microfluidic system to deliver semen to the microfluidic system; at least a second semen inlet disposed proximate to the second end and providing access to the microfluidic system to deliver semen to the microfluidic system; a chamber providing access to the microfluidic system disposed between the at least first semen inlet and the at least second semen inlet, the chamber including a top collection chamber that is greater than 3 mm in height and about 15 mm to about 30 mm in diameter for collecting sorted motile sperm from the microfluidic system, a bottom chamber about 15 mm to about 20 mm in diameter and 3 mm or less in height that is fluidly connected to the top collection chamber, and a microporous filter positioned between the top collection chamber and the bottom chamber; and a flow channel extending from the at least first semen inlet to the at least second semen inlet for delivered sperm to enter the bottom chamber and travel upward from the bottom chamber into the top collection chamber. In the system, the at least first semen inlet, the at least second semen inlet, and the chamber are fluidly connected to the flow channel, and the flow channel between the at least first semen inlet and the chamber and between the at least second semen inlet and the chamber is about 1 mm to about 10 mm in length, about 1 mm to about 3 mm in width, and about 100 μm to about 500 μm in height. In the system, the at least first semen inlet is about 0.1 mm to about 1.0 mm in diameter and 3 mm or less in height and is configured to also function as at least a first fluid outlet during use of the system. In the system, the at least second inlet is about 0.1 mm to about 1.0 mm in diameter and 3 mm or less in height and is configured to also function as at least a second fluid outlet during use of the system. In the system, the greater height of the chamber relative to the at least first and second semen inlets provides for a first fluid flow from the top collection chamber downward to the bottom chamber during use of the system. In some embodiments of the system, the flow channel across the bottom chamber is about 15 mm to about 30 mm in diameter and greater than 6 mm in height. In the system, the housing can include PDMS, PMMA, a plastic, or combination thereof. In the system, the chamber can be substantially elliptical or substantially cylindrical. The system can further include three or more (e.g., 3, 4, 5, 6, 7, 8, 9, 10) semen inlets. The system can include one or both of a pipette and tubing operably and fluidly connected to at least one of the at least first and second semen inlets for delivering semen. The system can further include (e.g., when in use) semen and a fluid including a sperm preparation buffer. The system can further include a heating system to maintain a temperature of 37° C. In the system, the microporous filter includes a plurality of micropores sized to permit a head of a sperm to pass therethrough.

Additionally described herein is a method for sorting sperm that includes: providing a system for sorting sperm according to the embodiments described in the paragraph above; delivering a sample of semen or sperm to at least one of the at least first and second semen inlets; delivering a sufficient amount of fluid to the top collection chamber such that the top collection chamber is filled with the fluid resulting in a first fluid flow from the top collection chamber downward to the bottom chamber such that motile sperm travel against the first fluid flow upward from the bottom chamber through the microporous filter to the top collection chamber; and harvesting motile sperm that have passed through the microporous filter and entered the top collection chamber. In the method, harvesting motile sperm that have passed through the microporous filter and entered the top collection chamber can include collecting the motile sperm with a pipette. In the method, delivering a sufficient amount of fluid to the top collection chamber can include delivering the fluid from a syringe, tube, pipette or combination thereof. In the method, a second fluid flow including waste fluid travels away from the bottom chamber and towards the at least first semen inlet and the at least second semen inlet, and the method can further include removing waste fluid from the at least first and second fluid outlets at one or more time points or continuously after delivering the sample of semen or sperm. The method can further include heating the system for sorting sperm to maintain a temperature of 37° C.

As used herein, the term "microfluidic" means manipulating fluid in microliters volumes. The term "microfluidic chip" is a device having one or more channels for processing or movement of a microliter or microliters amount of fluid.

By the term "waste fluid" is meant any fluid that contains semen plasma, dead, and/or dying sperm cells.

The terms "patient," "subject" and "individual" are used interchangeably herein, and mean a subject, typically a mammal, to be treated, diagnosed, and/or to obtain a biological sample (semen sample) from. Subjects include, but are not limited to, humans, non-human primates, horses, cows, sheep, pigs, rats, mice, dogs, and cats. Semen and sperm samples include those that have been manipulated in any way after their procurement, such as by centrifugation, filtration, treatment with reagents, washing, or enriched for certain cell populations. A semen sample or sperm sample encompass a clinical sample, and also include cells in culture and cell supernatants. Such samples may include fresh-frozen samples.

Although systems and methods similar or equivalent to those described herein can be used in the practice or testing of the present invention, suitable systems and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Figure 1A:
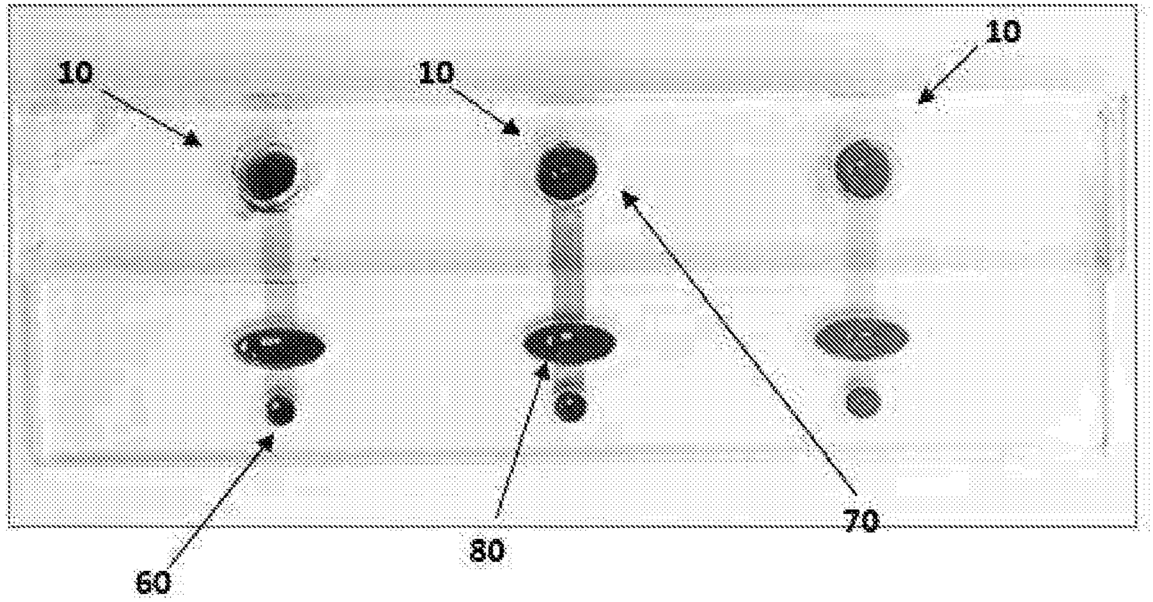
FIG. 1A is a photograph of a top view of one embodiment of a system for sperm selection as described herein. In this photograph, three identical systems are lined up in series such that in each system, a sperm inlet chamber is at the top, a flow inlet is at the bottom, and a collection chamber is positioned between the sperm inlet chamber and the flow inlet.

Systems and methods for sorting sperm are provided. The systems include a housing and a microfluidic system supported by the housing. The systems also include two or more inlets providing access to the microfluidic system to deliver sperm or semen and fluid to the microfluidic system, as well as an outlet for harvesting sorted sperm. The microfluidic system includes a flow channel that provides a flow path for sperm from an inlet to an outlet while sperm travels against a fluid flow towards an outlet for harvesting. In the systems, fluid delivered to the microfluidic system via an inlet flows from the inlet towards one or more outlets, and the flow channel extending along the length of the microfluidic system provides a flow path for motile sperm to travel against the fluid flow towards a collection outlet for harvesting. In some embodiments of a system, the microfluidic system also includes a microporous filter arranged in the flow path between the inlet and the collection outlet to cause motile sperm traveling against the fluid flow to pass through the filter to reach the collection outlet for harvesting. The microfluidic systems described herein exploit sperm rheotaxis for sorting motile sperm from non-motile or insufficiently motile sperm. In the experiments described below, the microfluidic systems were tested under various physiologically relevant flow conditions. It was discovered that at certain flow rates, sperm actively orient and swim against the flow. Sperm that exhibited positive rheotaxis showed better motility and velocity than the control (no-flow condition). In natural sperm selection, sperm has to travel a long distance against fluid flow before standing a chance for fertilization. To quantitatively investigate the effect of fluid flow on sperm guidance in vitro, microfluidic devices were developed and tested and it was found that the optimal flow rate to sort sperm based on rheotaxis is 0.5-4 μL/min (5.1-40.4 pN drag force) as more than 60% of sperm show rheotaxis at such flow conditions. Considering the capability of the developed microfluidic devices described herein to handle small to large semen volumes, these sperm sorting microfluidic devices can be used for all of the IUI, IVF and ICSI procedures, including sperm selection during, for example, ART procedures, mimicking natural sperm selection. An advantage of the present invention is that the sperm cells to be sorted are washed during the sorting process, as only motile healthy cells can travel against the flow and dead/less functional sperm cells and debris cannot move against the flow direction. With 40-50% of infertility cases being caused by male infertility, it is important to develop methods to sort and select healthy sperm based on natural sperm guidance mechanisms, without the risk of damages and defects produced by centrifugation-based sorting systems currently used in clinical laboratories. In addition, the systems and microfluidic devices described herein have applicability beyond human fertility including biodiversity and conservation of endangered or rare species.

Figure 1B:
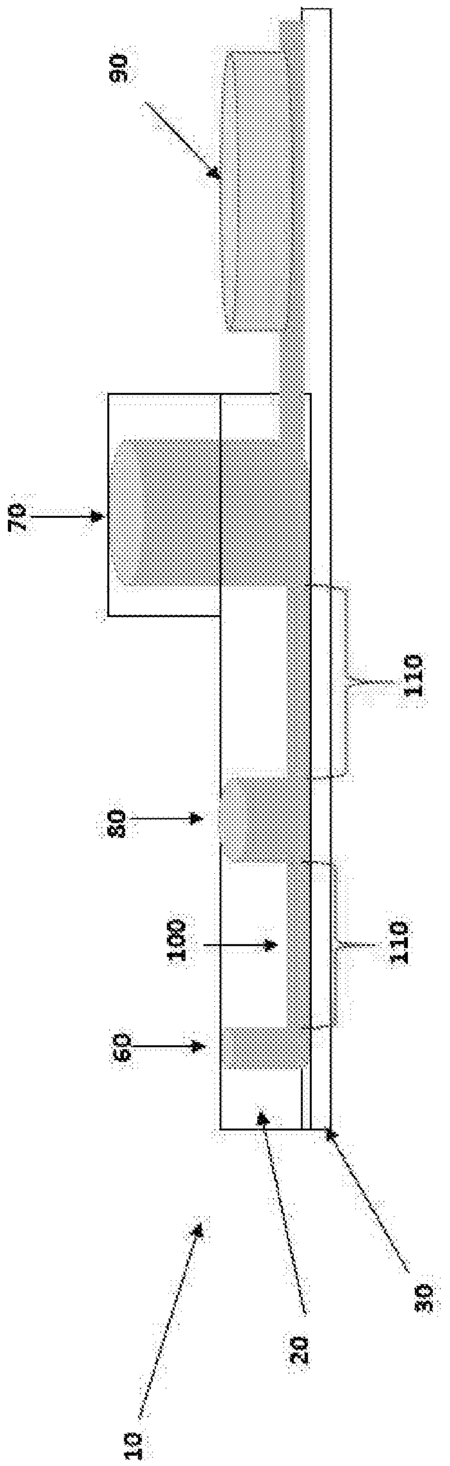
FIG. 1B is a side (profile) view of one embodiment of a system for sperm selection as described herein.

Referring to FIG. 1A and FIG. 1B, a sperm sorting system is illustrated. The system 10 includes a flexible housing 20 operably connected to a substrate 30 having a first end 40 and a second end 50. The housing 20 can be, for example, polydimethylsiloxane (PDMS), poly-(methyl methacrylate) (PMMA), a flexible plastic, or combination thereof. The housing 20 can be any material that is flexible and non-toxic to sperm cells. In typical embodiments of system 10, the substrate 30 is a glass slide. However, the substrate can be any material that is transparent. The system 10 also includes a microfluidic system supported by the flexible housing 20; a first inlet 60 positioned proximate to the first end 40 and providing access to the microfluidic system to deliver fluid to the microfluidic system; a second inlet 70 disposed distal to the first end 40 and providing access to the microfluidic system to deliver sperm to the microfluidic system; an outlet 80 that includes a collection chamber providing access to the microfluidic system to collect sorted sperm from the microfluidic system, the outlet 80 disposed between the first inlet 60 and the second inlet 70; a waste chamber 90 providing access to the microfluidic system for collecting waste fluid from the microfluidic system disposed proximate to the second end 50; and a flow channel 100.

The flow channel 100 extends from the first inlet 60 to the waste chamber 90 and provides a flow path for sperm to travel from the second inlet 70 to the collection chamber within the outlet 80 against a fluid flow from the first inlet 60 to the waste chamber 90. The first inlet 60, the second inlet 70, the outlet 80, and the waste chamber 90 are all fluidly connected to the flow channel 100 such that fluid flows 110 between the first inlet 60 and the outlet 80, and between the outlet 80 and the second inlet 70, at a speed higher than fluid flows along all other points of the flow channel 100. The dimensions of the flow channel 100 (and of the inlets and outlets) are such that when fluid is flowing along the flow channel 100, the fluid flow speed is greater in between the first inlet and the outlet (110) and between the second inlet and the outlet (110) than it is when flowing through the outlet 80 and through the second inlet 70. The dimensions of the flow channel 100 are about 1 mm-50 mm (e.g., 0.9 mm, 1.0 mm, 10 mm, 20 mm, 30 mm, 40 mm, 49 mm, 50 mm, 51 mm) in length, about 1 mm to 20 mm (e.g., 0.9 mm, 1.0 mm, 2.0 mm, 3.0 mm, 4.0 mm, 5.0 mm, 6.0 mm, 7.0 mm, 8.0 mm, 9.0 mm, 10.0 mm, 11.0 mm, 12.0 mm, 13.0 mm, 14.0 mm, 15.0 mm, 16.0 mm, 17.0 mm, 18.0 mm, 19.0 mm, 20.0 mm, 21.0 mm) in width, and about 25 μm to 250 μm (e.g., 24 μm, 25 μm, 50 μm, 100 μm, 150 μm, 200 μm, 250 μm, 251 μm) in height. The outlet 80 that includes a collection chamber is designed to collect the motile sperm from a sperm or semen sample (fresh or frozen) delivered to the second inlet 70 that were able to travel against the fluid flow 110 in the flow channel 100 and upwards into the outlet 80 and specifically into the upper portion of the outlet 80 which is the collection chamber for collection and harvesting. In this system, the fluid flow 110 prevents non-motile sperm, dead sperm and debris from traveling from the second inlet 70 to the collection chamber within the outlet 80, thus efficiently and reliably sorting motile sperm.

In the system 10, the first inlet 60 is generally cylindrical and about 0.5 mm-1.5 mm (e.g., 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm) in diameter and about 1.5 mm-3 mm (e.g., 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm) in height. The second inlet 70 is generally cylindrical and about 3 mm-20 mm (e.g., 2.9 mm, 3.0 mm, 4.0 mm, 5.0 mm, 6.0 mm, 7.0 mm, 8.0 mm, 9.0 mm, 10.0 mm, 11.0 mm, 12.0 mm, 13.0 mm, 14.0 mm, 15.0 mm, 16.0 mm, 17.0 mm, 18.0 mm, 19.0 mm, 20.0 mm, 21.0 mm) in diameter and about 1.5 mm-3 mm (e.g., 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm) in height. The outlet 80 (comprising a collection chamber) is typically elliptical, but in some embodiments is cylindrical. In some embodiments, the outlet 80 is elliptical having the dimensions: about 5 mm-11 mm (e.g., 4.9 mm, 5.0 mm, 6.0 mm, 7.0 mm, 8.0 mm, 9.0 mm, 10.0 mm, 11.0 mm, 11.1 mm)×2.5 mm (e.g., 2.2 mm, 2.3 mm, 2.4 mm, 2.5 mm, 2.6 mm, 2.7 mm) elliptical and about 1.5 mm-3 mm (e.g., 1.4 mm, 1.5 mm, 2.0 mm, 2.5 mm. 3.0 mm, 3.1 mm) in height. The waste chamber 90 is typically cylindrical and about 25 mm-200 mm (e.g., 24.0 mm, 25.0 mm, 30.0 mm, 50.0 mm, 75.0 mm, 100 mm, 125 mm, 150 mm, 175 mm, 200 mm, 201 mm, 205 mm) in diameter and 1.5 mm-3 mm (e.g., 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm) in height. The heights of the first inlet 60, the second inlet 70, the outlet 80 and the waste chamber 90 can be identical, substantially identical, or different. In the embodiment shown in FIG. 1B, the second inlet 70 has a greater height than the first inlet 60, the outlet 80, and the waste chamber 90.

The dimensions of the systems given above are such that optimal flow rates for sperm rheotaxis are achieved, i.e., particular flow rates at which sperm actively orient and swim against the flow. From the sperm rheotaxis experiments described below, the best flow rate determined was less than 6 μL/min, e.g., 0.5-4 μL/min (0.4 μL/min, 0.5 μL/min, 1 μL/min, 2 μL/min, 3 μL/min, 4 μL/min) (5.1-40.4 pN drag force) as more than 60% sperm show rheotaxis at such flow conditions.

When in use, system 10 includes a semen or sperm sample and an appropriate fluid such as a sperm preparation buffer. An appropriate fluid is any that keeps the sperm viable (maintains/supports cell viability) and does not affect sperm quality; such fluids are used in sperm preparation and washing. One example of a sperm preparation buffer is Human Tubal Fluid (HTF-HEPES)+1% Bovine Serum Albumin (BSA) or Human Serum Albumin (HSA) (HTF+BSA/HAS). System 10 can further include a material or apparatus for delivering fluid to the microfluidic system. In a typical embodiment, a syringe, a syringe pump, and tubing are operably and fluidly connected to the first inlet 60 for delivering fluid. However, any suitable material or apparatus can be used for delivering fluid. Systems of sorting sperm can also include devices and apparatuses for imaging sperm. In the experiments described below, for imaging sperm, an optical microscope was used and sperm tracks were analyzed using ImageJ CASA plugin. The light source was a part of the microscope. Any standard microscope can be used. Any suitable hardware and apparatuses can be used for observing, filming, and counting sperm, e.g., a microscope camera. Any other suitable image sensor, imaging device, optical detector, light source, and combination thereof, can be used in the systems and methods described herein. The selection of an appropriate software program is within the ordinary skill of the art. For example, IC Capture software (The Imaging Source, Charlotte, NC) can be used. Any software suitable for bright field imaging can be used in the systems and methods described herein. In the experiments described below, an external heated stage/surface was used to maintain the temperature at 37° C. Any suitable heating source can be incorporated in the methods and systems described herein.

Fabrication of the systems and microfluidic systems described herein is described in Example 2 below. This methodology is also described in detail in U.S. patent application Ser. No. 15/037,844 incorporated herein by reference in its entirety.

Methods for sorting sperm are described herein. In one embodiment, a method for sorting sperm includes providing system 10 of FIG. 1B. In the method, a suitable amount of fluid (e.g., sperm preparation buffer) is delivered to the first inlet 60 of the system 10 for sorting sperm such that the microfluidic system is substantially filled with fluid. The fluid is continued to be delivered and the fluid's flow rate is increased to about 10 μl/minute or greater, whereby the fluid flows from the first inlet 60 to the waste chamber 90 resulting in a flow path. The fluid flows between the first inlet 60 and the outlet 80, and between the outlet 80 and the second inlet 70, at a speed higher than fluid flows along all other points of the flow channel (see reference number 110 in FIG. 1*b* for areas of the flow channel 100 where fluid flows at a higher speed). After the fluid's flow rate is increased, a sample including sperm is delivered to the second inlet 70 of the system 10 for sorting sperm. In this method, the flow rate of 10 μl/minute or greater prevents sperm delivered to the second inlet 70 from entering the collection chamber 80. In a typical embodiment, the flow rate is lowered to a rate of 0.5 μl/minute or above to about 8 μl/minute for a suitable period (e.g. about 15 to about 75 minutes) of time such that motile sperm travel against the fluid flow and enter the collection chamber (within outlet 80). After motile sperm have entered the collection chamber (within outlet 80) they are harvested from the collection chamber. In the method, only motile healthy cells can travel against the flow into the collection chamber; less functional sperm cells, dead sperm cells and debris cannot move against the flow direction. In a typical embodiment of this method, harvesting motile sperm that have entered the collection chamber within outlet 80 includes pinching or compressing at least a portion of the flexible housing 20 adjacent to sides of the collection chamber within outlet 80 while harvesting the sperm. PDMS is a flexible material and when incorporated in the housing and microchannels, they can be pinched (compressed) to block the flow channel during the sperm collection step. Such "channel blocking" prevents the sperm from the sperm inlet chamber (second inlet 70 in system 10) becoming mixed with sorted sperm, preventing unsorted sperm from mixing with the sorted sperm population. When delivering a suitable amount of fluid to the first inlet 60 a syringe, a syringe pump, and tubing that is operably and fluidly connected to the first inlet 60 can be used. However, any suitable device, apparatus or material can be used to delivered fluid to the microfluidic system. In some embodiments, the method further includes imaging the sperm as they travel against the fluid flow and enter the collection chamber (within outlet 80) and/or applying or providing heat to the system to maintain a temperature of 37° C.

Figure 2:
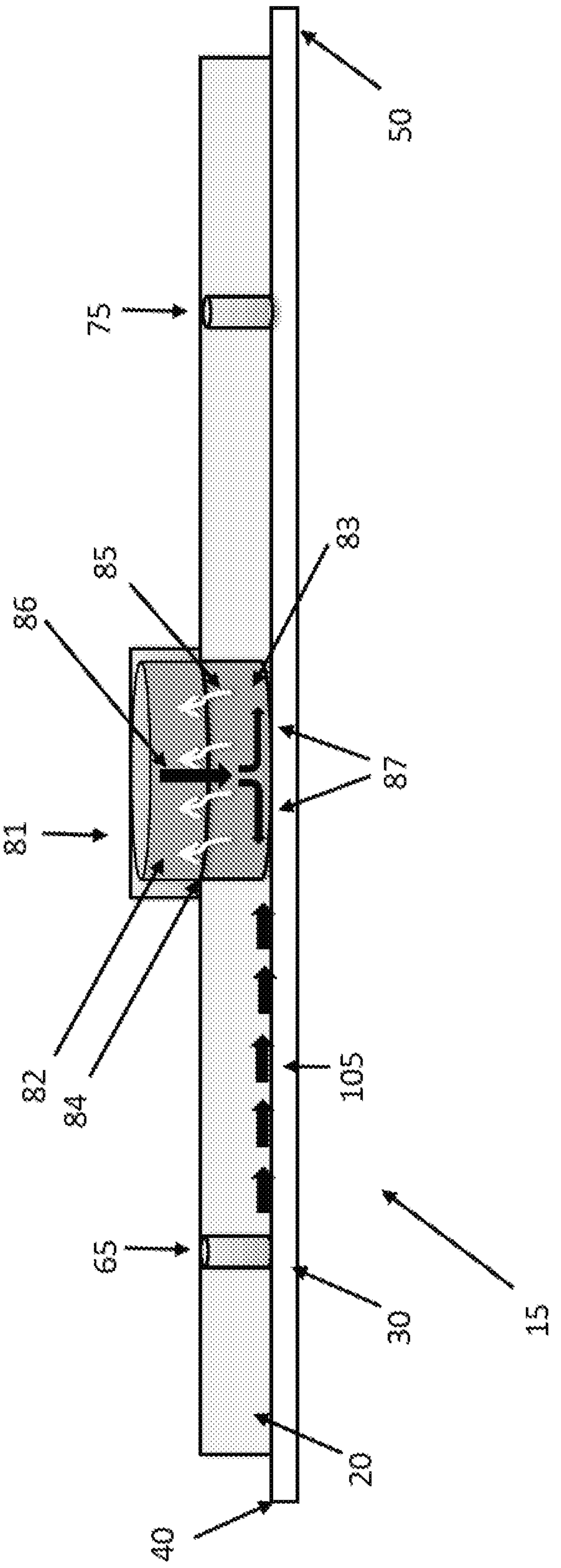
FIG. 2 is a side view of another embodiment of a system for sperm selection that includes a filter.

Referring to FIG. 2, another embodiment of a system for sorting sperm is illustrated. The system 15 includes a housing 20 operably connected to a substrate 30 having a first end 40 and a second end 50. The housing 20 can be, for example, PDMS, PMMA, a plastic, or combination thereof. The housing 20 can be flexible, rigid, semi-rigid, or a combination thereof. The housing 20 can be any material that is non-toxic to sperm or other (e.g., mammalian) cells. In typical embodiments of system 15, the substrate 30 is a glass slide. However, the substrate 30 can be any material that is transparent. The system 15 also includes a microfluidic system supported by the housing 20; at least a first semen inlet 65 positioned proximate to the first end 40 and providing access to the microfluidic system to deliver semen to the microfluidic system; at least a second semen inlet 75 disposed proximate to the second end 50 and providing access to the microfluidic system to deliver semen to the microfluidic system; and a chamber 81 providing access to the microfluidic system disposed between the at least first semen inlet 65 and the at least second semen inlet 75. Chamber 81 can be elliptical, substantially elliptical, cylindrical, and substantially cylindrical. Within chamber 81 is a top collection chamber 82, a bottom chamber 83, and a microporous filter sandwiched (disposed or positioned) between the top collection chamber 82 and the bottom chamber 83. Top collection chamber 82 is fluidly connected to bottom chamber 83 and is designed to collect the motile sperm 85 from a sperm or semen sample (fresh or frozen) delivered to at least the first semen inlet 65 that were able to travel upwards from the bottom chamber 83 against the first fluid flow 86 from the top collection chamber 82 and through the microporous filter 84 into the top collection chamber 82. The top collection chamber 82 is greater than 3 mm in height (e.g., 3.1 mm, 3.2 mm, 3.3 mm, 3.4 mm, 3.5 mm, 3.6 mm, 3.7 mm, 3.8 mm, 3.9 mm, 4.0 mm, 4.1 mm, etc.) and about 15 mm to 30 mm (e.g., 14 mm, 15 mm, 20 mm, 25 mm, 30 mm, 31 mm, etc.) in diameter and is for collecting sorted motile sperm. The bottom chamber 83 is about 15 mm-20 mm (e.g., 14 mm, 15 mm, 16 mm, 17 mm, 18 mm, 19 mm, 20 mm, 21 mm) in diameter and 3 mm or less (e.g., 3 mm, 2.9 mm, 2.8 mm, 2.7 mm, 2.6 mm, 2.5 mm, 2.4 mm, 2.3 mm, 2.2 mm, 2.1 mm, 2.0 mm, 1.9 mm) in height The system 15 also includes a flow channel 105 extending from the at least first semen inlet 65 to the at least second semen inlet 75; semen is injected into at least one of the at least first semen inlet 65 and the at least second semen inlet 75, and sperm within the semen travel along the flow channel 105 from at least the at least first semen inlet 65 to the bottom chamber 83, optionally from the at least second semen inlet 75 to the bottom chamber 83, and upward from the bottom chamber 83 into the top collection chamber 82 against the first fluid flow 86. In FIG. 2, the second fluid flow 87 is waste fluid that travels away from chamber 81 and towards the at least first semen inlet 65 and the at least second semen inlet 75 (in use, waste liquid is removed from the at least first and second semen inlets 65, 75 which function as fluid outlets for removing waste fluid). The at least first semen inlet 65, the at least second semen inlet 75, and the chamber 81 are fluidly connected to the flow channel 105.

The flow channel 105 between the at least first semen inlet 65 and the chamber 81 and between the at least second semen inlet 75 and the chamber 81 is about 1 mm-10 mm (e.g., 0.9 mm, 1.0 mm, 1.5 mm, 2.0 mm, 2.5 mm, 3.0 mm, 3.5 mm, 4.0 mm, 4.5 mm, 5.0 mm, 5.5 m, 6.0 mm, 6.5 mm, 7.0 mm, 7.5 mm, 8.0 mm, 8.5 mm, 9.0 mm, 9.5 mm, 10.0 mm, 10.1 mm, 10.5 mm, 11 mm) in length, about 1 mm-3 mm (e.g., 0.9 mm, 1.0 mm, 1.5 mm, 2.0 mm, 2.5 mm, 3.0 mm, 3.1 mm, 3.2 mm, 3.3 mm) in width, and 100 μm-500 μm (99 μm, 100 μm, 150 μm, 200 μm, 250 μm, 300 μm, 350 μm, 400 μm, 450 μm, 500 μm, 501 μm, 510 μm, 550 μm) in height. The flow channel 105 across the bottom chamber 83 is 15 mm-30 mm (e.g., 14.8 mm, 14.9 mm, 15.0 mm, 18.0 mm, 20.0 mm, 25 mm, 29 mm, 30 mm, 31 mm) in diameter and greater than 6 mm (e.g., 6.1 mm, 6.2 mm, 6.3 mm, 6.4 mm, 6.5 mm, 7.0 mm, 8.0 mm, 9.0 mm, 10.0 mm, 11.0 mm, 12.0 mm, 13.0 mm, 14.0 mm, 15.0 mm, 16.0 mm, 17.0 mm, 18.0 mm, 19.0 mm, 20 mm) in height.

In the system 15, the height of the chamber 81 is greater than the heights of the at least first and second semen inlets 65, 75. This height differential provides for a first fluid flow 86 from the top collection chamber 82 downward to the bottom chamber 83 and a second fluid flow 87 of waste fluid traveling to the at least first semen inlet 65 and to the at least second semen inlet 75 during use of the system 15. The at least first semen inlet 65 and the at least second semen inlet 75 are each 0.1 mm-1.0 mm (e.g., 0.09 mm, 0.1 mm, 0.2 mm, 0.3 mm, 0.4 mm, 0.5 mm, 0.6 mm, 0.7 mm, 0.8 mm, 0.9 mm, 1.0 mm, 1.1 mm) in diameter and 3 mm or less (e.g., 3 mm, 2.9 mm, 2.8 mm, 2.7 mm, 2.6 mm, 2.5 mm, 2.4 mm, 2.3 mm, 2.2 mm, 2.1 mm, 2.0 mm, 1.9 mm) in height. The at least first semen inlet 65 and the at least second semen inlet 75 are configured to also function as fluid outlets (at least a first fluid outlet and at least a second fluid outlet, respectively) during use of the system. In some embodiments, the system includes three or more semen inlets (e.g., 3, 5, 5, 6, 7, 8, 9, 10). The microporous filter 84 sandwiched between the top collection chamber 82 and the bottom chamber 83 comprises a plurality of micropores sized to permit a head of a sperm to pass therethrough to facilitate sorting motile sperm from less-motile or non-motile sperm. The micropores typically have a size of at least 5 μm and less than 50 μm. A polycarbonate microporous filter is typically used, but any suitable microporous filter can be used.

A system 15 can include at least one of: a pipette and tubing operably and fluidly connected to at least one of the at least first and second semen inlets 65, 75 for delivering semen. Prior to, during and after use, system 15 can include semen (e.g., a semen sample) and a fluid including a sperm preparation buffer (e.g., HTF-HEPES+1% BSA or HSA (HTF+BSA/HAS)). The system 15 may also include a heating system to maintain temperature.

In an embodiment of a method for sorting sperm using the system 15 of FIG. 2, the method includes providing the system 15; delivering (e.g., injecting) a sample of semen or sperm into at least one of the at least first and second semen inlets 65, 75 such that sperm enter the bottom chamber 83 for sorting; delivering a sufficient amount of fluid to the top collection chamber 82 such that the top collection chamber 82 is filled with the fluid resulting in a first fluid flow 86 from the top collection chamber 82 downward to the bottom chamber 83 such that motile sperm travel against the first fluid flow 86 and through the microporous filter 84 and enter the top collection chamber 82; and harvesting motile sperm 85 that have passed through the microporous filter 84 and entered the top collection chamber 82. In the method, motile sperm 85 that have passed through the microporous filter 84 and entered the top collection chamber 82 can be harvested using any suitable method and/or apparatus. In the experiments described below, motile sperm 85 were harvested using a pipette. To deliver a sufficient amount of fluid to the top collection chamber 81, any suitable method or apparatus can be used, for example, fluid can be delivered using a syringe, tube or pipette or combination thereof. Fluid can be delivered manually or robotically such that fluid input does not allow significant mixing of injected fluid with fluid in bottom chamber 83. When system 15 is in use during sperm sorting, fluid is being removed from the at least first and second fluid outlets (at least first and second semen inlets 65, 75) in order to collect waste fluid containing semen plasma, debris, dead/dying and less functional sperm. Fluid can be removed using any suitable method and apparatus, e.g., a pipette. Fluid can be removed continuously from the at least first and second fluid outlets, or it can be removed at one or more distinct time points. The method typically includes heating the system 15 for maintaining a temperature of 37° C. using any suitable heating source.

EXAMPLES

The present invention is further illustrated by the following specific examples. The examples are provided for illustration only and should not be construed as limiting the scope of the invention in any way.

Example 1—Systems for Sorting Sperm

The present invention recognizes that sperm travel from the uterus to the oocyte during the natural selection process against the fluid flow that flows in an opposite direction to sperm. The present invention recognizes and utilizes sperm rheotaxis as a mechanism for sorting sperm and has been experimentally demonstrated to leverage rheotaxis to sort healthy sperm. Specifically, the present invention provides a sperm sorting system to efficiently, reliably, and successfully sort sperm. As will be described, healthy motile sperm are fully collected at the outlet(s) post-sorting. These systems improve the efficiency of the sperm selection process, thereby controlling against DNA fragmentation, accumulation of debris, and generation of ROS as semen plasma and dead/dying cells are washed away during the sorting process.

Computational Analysis

Figure 4:
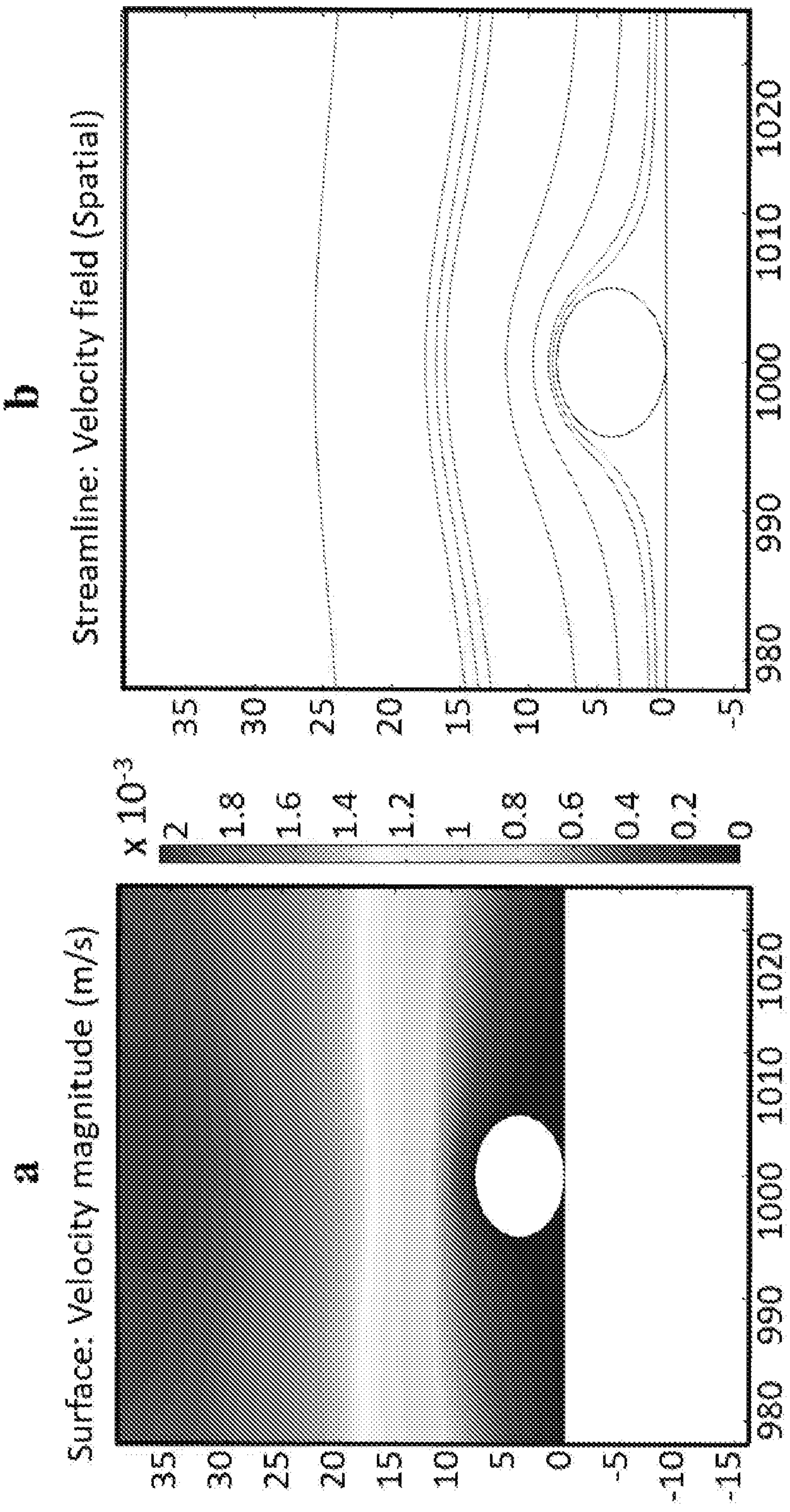
FIG. 4A is a simulated flow velocity representation inside a microfluidic system as described herein.
FIG. 4B shows streamlines for the velocity field of FIG. 4A.
FIG. 4C is a graphical representation of the relationship between various flow rates and drag force applied to the sperm inside a microfluidic channel.
Figure 4:
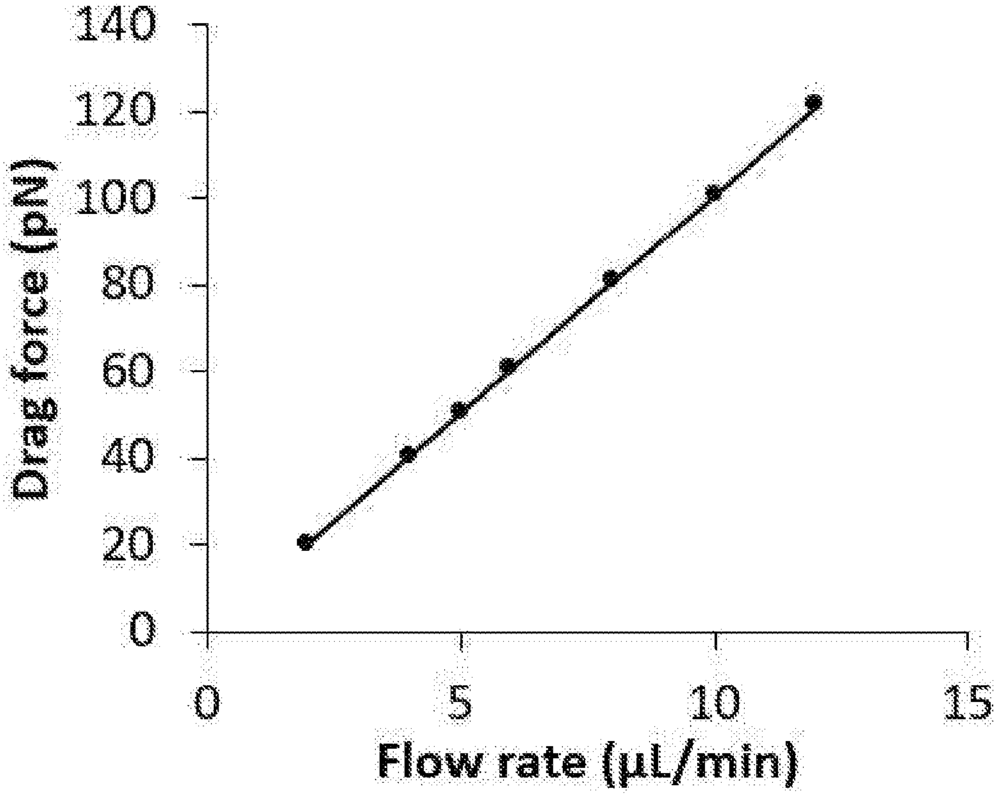

COMSOL simulations were performed to determine the effects of shear stress on sperm cells in the systems for sorting sperm described herein. A single sperm was modeled as an oval shaped structure with length 5 μm and width 4 μm. A microfluidic channel with a length of 28 mm and height of 76 μm was modeled and laminar flow conditions were assumed. The no-slip boundary conditions were applied to the walls of the microfluidic channel. Various flow rates resulted in different average velocities. A boundary condition with zero pressure was assumed for the outlet. The Navier-Stokes equations were used to simulate the motion of fluid passing by the sperm. Different sizes of meshes were applied to solve the simulation and velocity and pressure profiles were calculated. The velocity magnitude and streamlines are shown in FIG. 4A and FIG. 4B, respectively. The shear stress was calculated at various flow rates (2, 4, 5, 6, 8, 10, 12 μL/min) and the resultant drag force was determined (FIG. 4C). It was observed that the higher flow rates resulted in increased drag force that impedes the forward movement of sperm against the flow.

Quantitative Sperm Response to Various Flow Conditions

Figure 5:
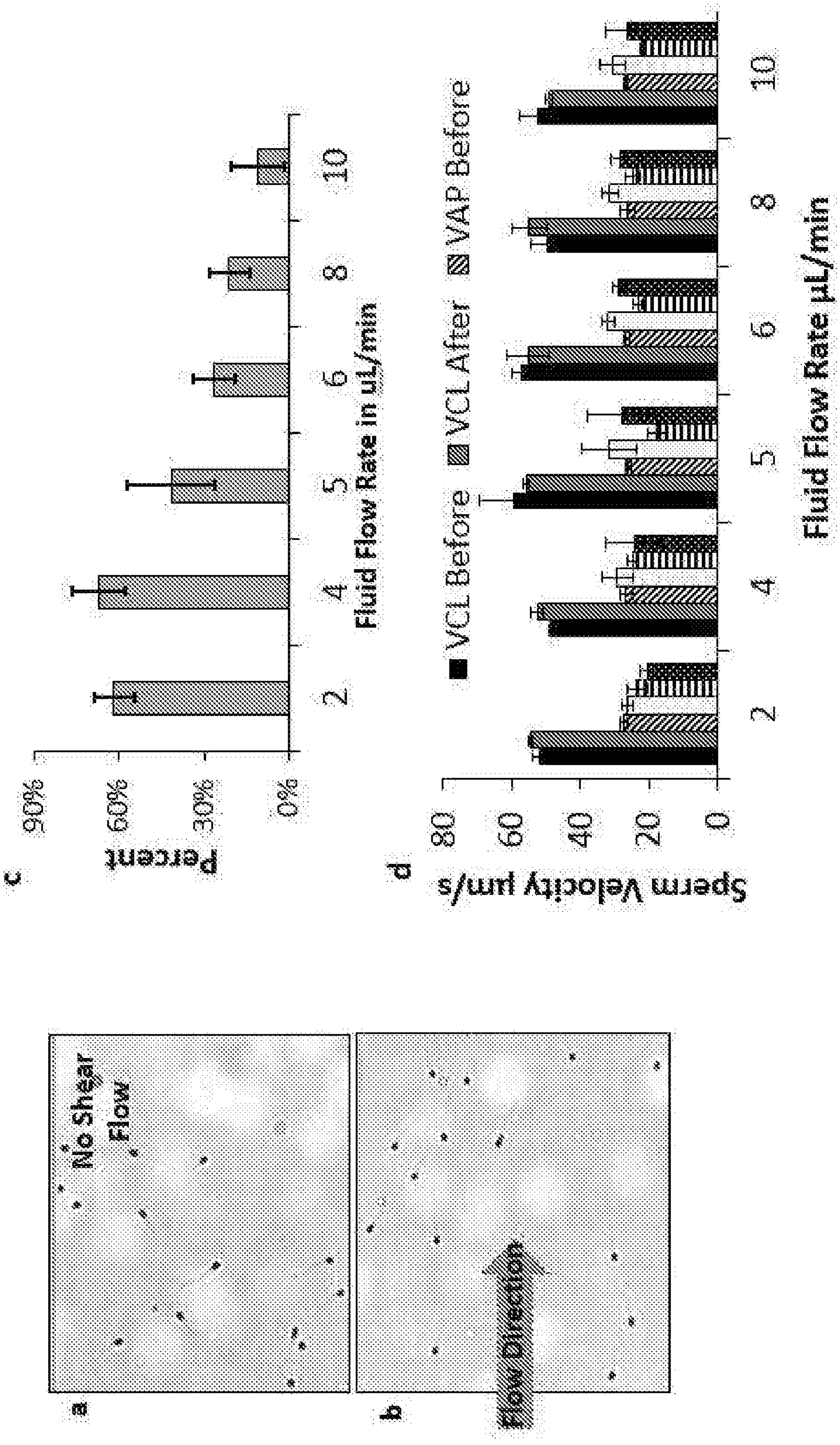
FIG. 5A is an image from a sperm motion video recorded using a microscope camera. The image shows the sperm position before flow in an embodiment of a system for sperm selection as described herein.
FIG. 5B is an image from a sperm motion video showing that sperm orient and swim in a direction opposite to flow.
FIG. 5C is a graph showing the percentage of sperm at different flow rates that oriented and progressively swam against flow. Data are shown as average±standard deviation. n=20-200, N=3. n: number of sperm, N: number of experiments.
FIG. 5D is a graph showing curvilinear velocity (VCL), average path velocity (VAP), and straight-line velocity (VSL) before and after flow in the system for sperm selection.
FIG. 5E is an image showing sperm paths before flow.
FIG. 5F is an image showing sperm paths during flow. Flow is from left to right.
Figure 5:
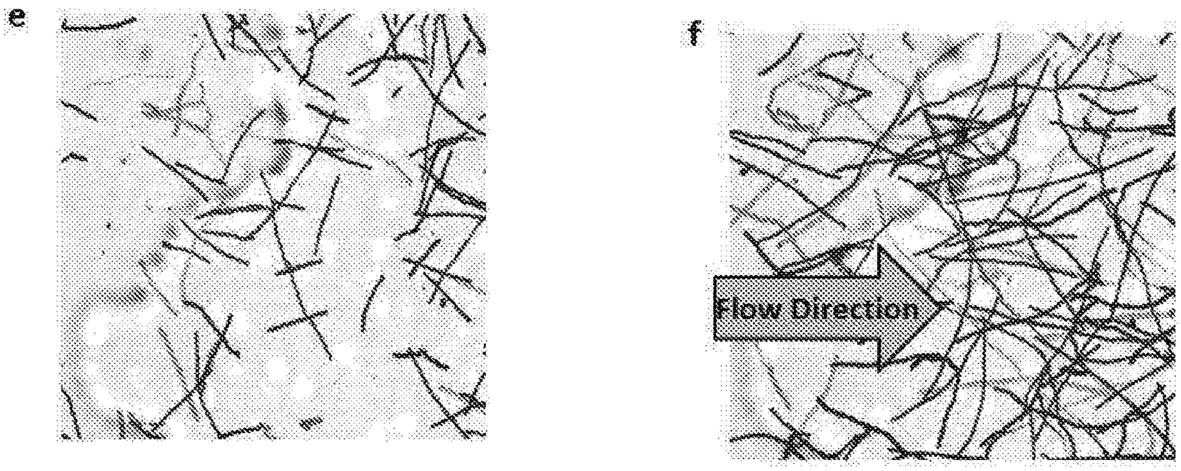

The effect of various flow conditions on sperm rheotaxis was investigated using a microfluidic device including only a flow inlet and a sperm inlet fluidly connected to a microfluidic channel supported by a glass slide. Sperm tracking videos were recorded in a microfluidic channel at before and after flow conditions. Sperm tracks and swimming directions were analyzed to determine the number of sperm that oriented and swam against the direction of flow at various flow rates (2 μL/min, 4 μL/min, 5 μL/min, 6 μL/min, 8 μL/min and 10 μL/min). Before the start of flow, sperm cells were moving randomly in all directions (FIG. 5A, 5E). After flow, the sperm cells oriented against the direction of flow (FIG. 5B, 5F). The percentage of sperm that orient their head and actively swim against the flow direction increases from 2 μL/min (61.85%±7.08%) to 4 μL/min (67.14%±9.63%) before steadily decreasing for the 5 μL/min (41.58%±15.28%), 6 μL/min (26.39%±7.59%), 8 μL/min (21.04%±6.89%), and 10 μL/min flow rates (10.95%±9.32%) (FIG. 5C). A one-way ANOVA showed these results to be significantly different across all groups ($p<0.05$). It was observed that at higher flow rates (10 μL/min and higher), almost all the sperm cells were unable to swim forward against the flow due to higher shear flow conditions.

Sperm motility parameters; curvilinear velocity (VCL), average path velocity (VAP) and straight-line velocity (VSL) were measured at before and after flow conditions. The sperm are tracked and their paths at before and after flow conditions were generated by the CASA plugin as seen in FIG. 5E and FIG. 5F, respectively. These sperm paths show the random linear progression of sperm that is normally exhibited in the absence of flow (FIG. 5E). The paths that are curved are a result of a sperm with its head facing downstream turning to head upstream (FIG. 5F). The squiggly paths are from sperm that were trying to swim but are being pushed back by the flow. No significant difference was observed in VCL, VAP and VSL between the six flow rates at before and after flow conditions ($p>0.05$) (FIG. 5D).

Sperm Showing Rheotaxis have Higher Progressive Motility

Figure 6:
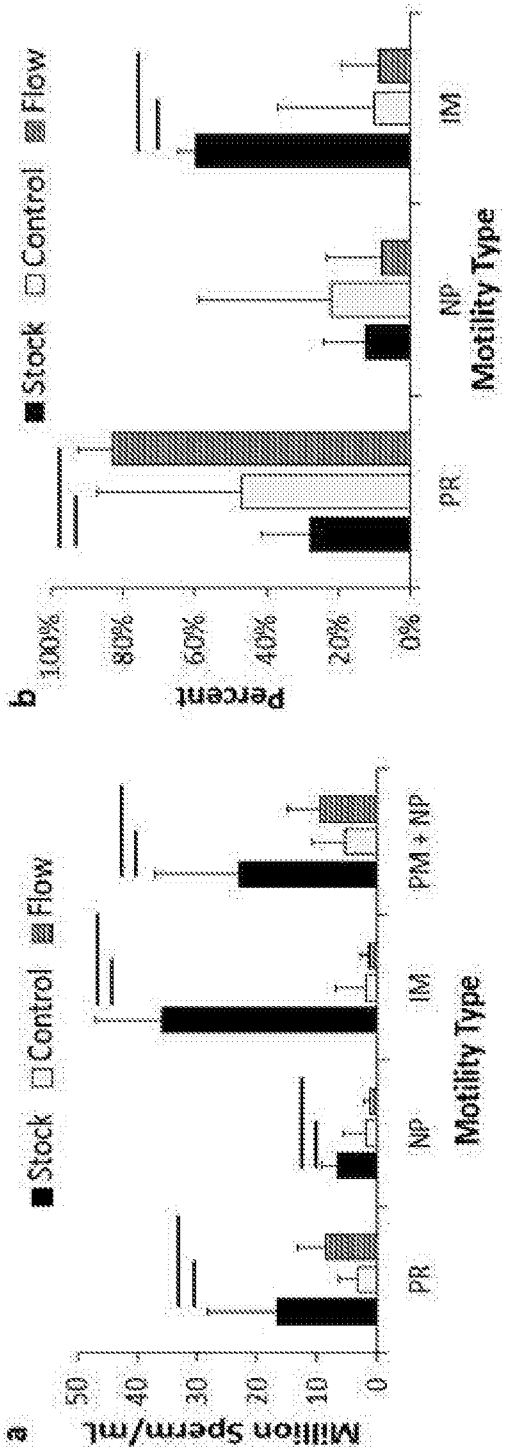
FIG. 6A is a graph showing the concentration of sperm in million sperm/mL and type of motility observed in each experimental group; (PR) progressive motility, (NP) non-progressive motility, (IM) immotility, and (PR+NP) total motility.
FIG. 6B is a graph showing the motility type of sperm recovered from a system for sperm selection as described herein; (PR) progressive motility, (NP) non-progressive motility, and (IM) immotility.
FIG. 6C is a graph showing the percent of sperm recovered from the collection chip after one hour; (M) motillity including non-progressive motility, and (PR) progressive motility.
FIG. 6D is a graph showing sperm VCL, VAP, and VSL for stock (raw semen sample), control, and flow sorted sperm. Flow rate used for all these results was 3 μL/min. Data are shown as average±standard deviation. The statistical significance between samples is marked with a straight line on the top of the graphs (p-value<0.05).
Figure 6:
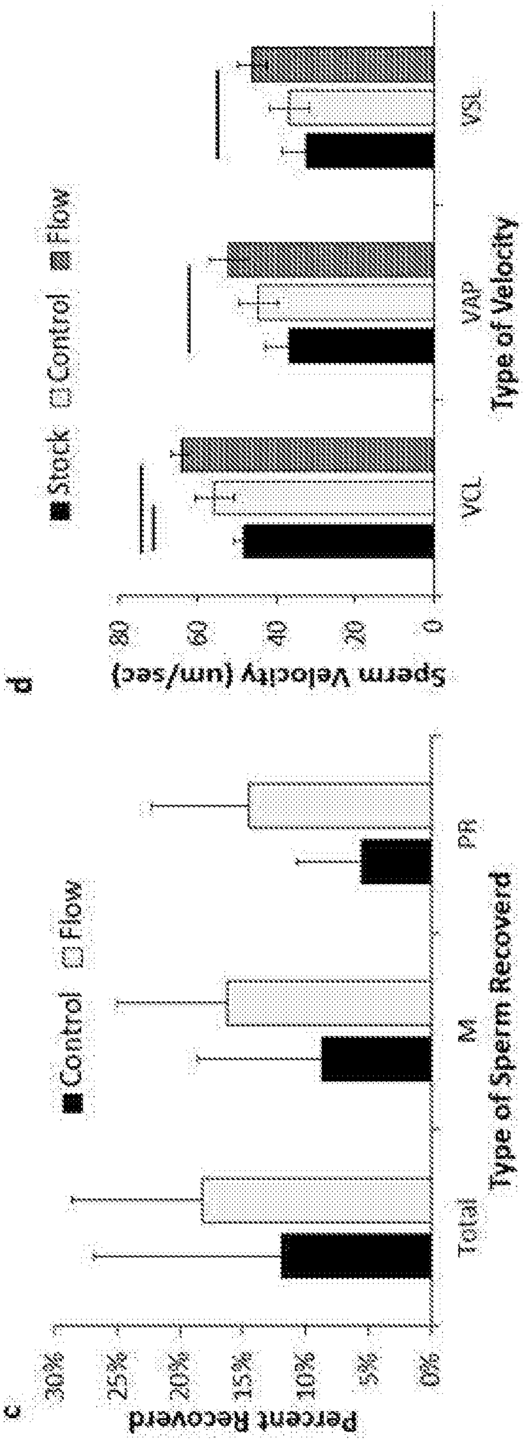

Concentration of sperm in million sperm/mL and type of motility was calculated in each experimental group; (PR) progressive motility, (NP) non-progressive motility, (IM) immotility, and (PR+NP) total motility (FIG. 6A). The total stock sperm (unsorted raw sperm sample) concentration ($59\pm17\times10^6$/mL) is significantly larger than both the control (no flow-condition) ($7.0\pm9.0\times10^6$/mL) and flow ($11\pm6\times10^6$/mL) concentrations ($p<0.05$). The stock concentration also has a significantly larger concentration of PR ($17\pm12\times10^6$/mL), NP ($6.5\pm3\times10^6$/mL), IM ($36\pm11\times10^6$/mL) and total motile ($23\pm14\times10^6$/mL) than the control and flow groups ($p<0.05$). The flow and control groups show no significant difference between their total concentration of sperm recovered after sorting ($p>0.05$), however the flow group does have a higher concentration of PR sperm ($8.6\pm4.5\times10^6$/mL) and total motile sperm ($9.6\pm5.210^6$/mL) than the no-flow control ($3.3\pm3\times10^6$/mL and $5.2\pm5.7\times10^6$/mL respectively) (FIG. 6A).

Sperm motility was assessed based upon motile, non-progressively motile and immotile. The average percentage of motile sperm for stock, control, and flow experimental group is 27.66%±11.43%, 46.85%±36.60% and 82.98%±15.06% respectively (FIG. 6B). The percent of motile sperm found in the flow group is significantly higher than that found in stock group ($p<0.05$). The total sperm motility (M+NP) in flow group was significantly higher (91.02%±9.49%) than stock (40.17%±13.68%) ($p<0.05$). The average percent of immotile sperm for stock, control and flow groups were 59.83%±13.68%, 9.95%±17.86%, and 8.98%+9.49% respectively. The stock has a significantly higher amount of immotile sperm compared to both the control and flow groups ($p<0.05$) (FIG. 6B).

The percent of sperm recovered from the control and flow group is 11.88%+14.94% and 18.26%±10.31%. The flow group has a larger recovery of motile (16.24%+8.78%) and progressively motile (14.54%±7.66%) sperm as compared to the control, whose values are 8.75%±9.75% and 5.54%±5.09% respectively (FIG. 4C), however the difference is statistically insignificant.

Sperm Showing Rheotaxis Have Higher Sperm Velocity Parameters

To determine the sperm swimming speed and linearity, the sperm kinematics need to be known. Sperm sorted in the flow group showed significantly higher values in VCL, VAP, VSL than the control and stock (FIG. 6D). The control VCL is also significantly larger than the stock. There is no significant difference between the linearity (describes path curvature) or the wobble (how many times the head crosses over the VAP).

Sperm Rheotaxis Using PDMS Flow Chip

Figure 7:
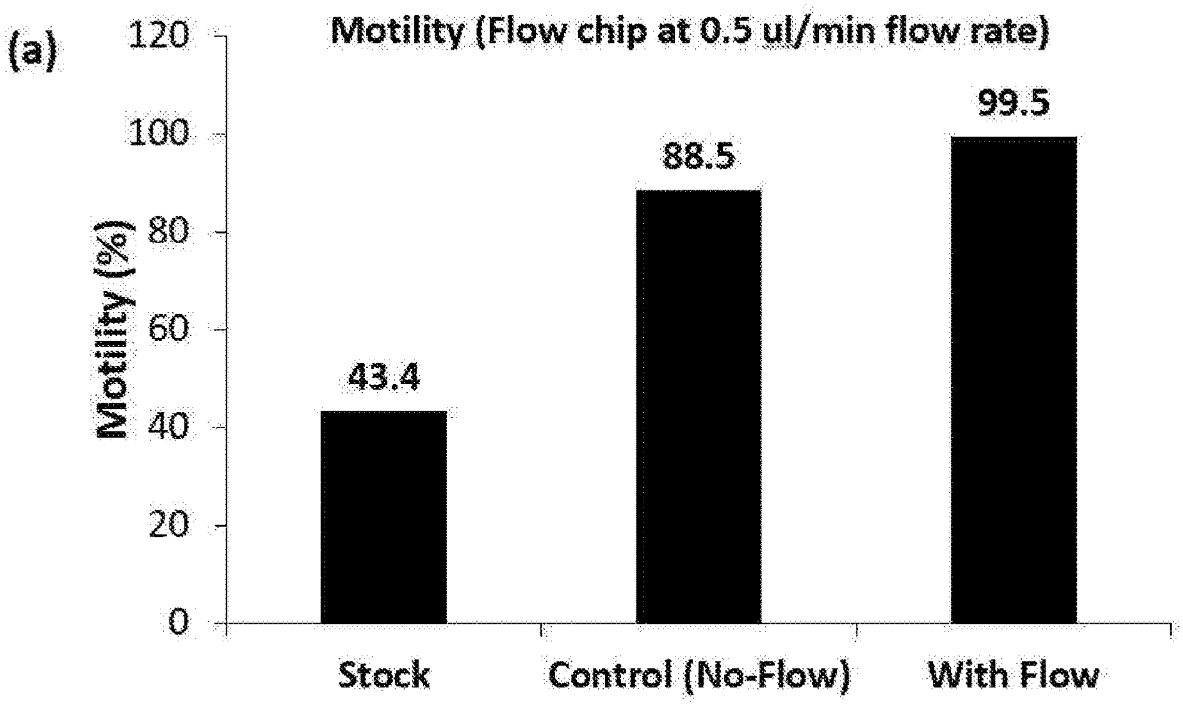
FIG. 7A is a graph showing motility of the sperm retrieved from a PDMS-based system for sperm selection embodiment (shown in profile in FIG. 1B) where buffer flows from outlet to inlet at a constant flow rate of 0.5 μl per min.
FIG. 7B is a graph showing motility of sperm retrieved from the collection chamber of systems for sperm selection that include a filter (shown in profile in FIG. 2). In this experiment, the filter-containing sperm selection system was designed such that the flow rate from the top collection chamber to the bottom chamber is 25 μl per min.
FIG. 7C is a graph showing the isolation efficiency of filter-containing sperm selection systems.
Figure 7:
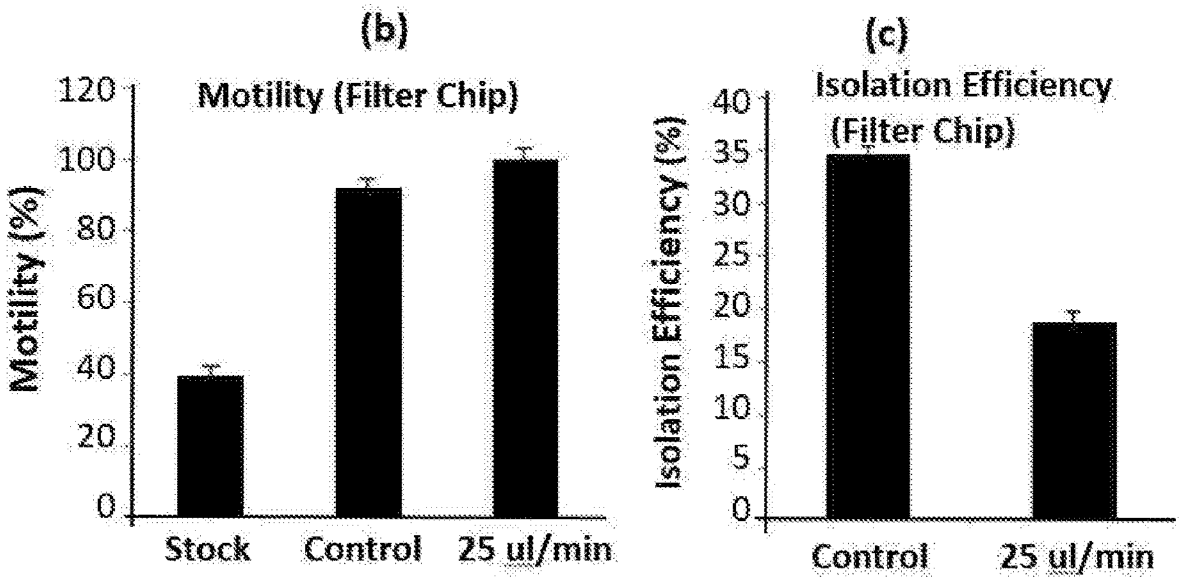

PDMS-based microfluidic devices in the systems for sorting sperm described herein were designed because PDMS is a flexible material and microchannels in the microfluidic devices can be pinched (compressed) to block the flow channel during the sperm collection step. Without channel blocking, the sperm from the sperm inlet chamber (second inlet 70 in system 10) can be mixed with sorted sperm, hence there are chances that unsorted sperm can be mixed with the sorted sperm population. A higher percent motility (99.5%) was observed of sperm retrieved from PDMS devices as compared to a control device (no flow, 88.5% motility) (FIG. 7A). This is a significant and superior improvement over aforementioned designs.

Sperm Rheotaxis Using Systems for Sorting Sperm

Systems for sorting sperm 15 having integrated microporous filters (FIG. 2, FIG. 3) were developed such that top collection chamber 82 has a greater height (i.e., is taller) to enable fluid flow from top collection chamber 82 down to bottom chamber 83. Sperm retrieved from the system for sorting sperm 15 show higher motility than from a control system 12 (which has no fluid flow), and stock (FIG. 7B). However, isolation efficiency was reduced in the system for sorting sperm 15 of FIG. 3 (right) compared to the control system of FIG. 3 (left) as less functional sperm are unable to swim against the flow to the top chamber (FIG. 7C).

Thus, systems and methods for sorting sperm are provided that are designed such that they do not require any centrifugation steps to retrieve healthy and motile sperm. The systems' design makes sperm sorting less labor-intensive and inexpensive. The systems exploit and utilize rheotaxis in microfluidic channels (flow channels) as a mechanism for sperm sorting. The systems can isolate motile and functional sperm that travel against the flow direction, mimicking the natural sperm selection process.

Example 2—Additional Embodiments of and Methods of Making a System for Sorting Sperm Device Fabrication To study the effect of fluid flow on sperm guidance, a microfluidic device including only a flow inlet and a sperm inlet fluidly connected to a microfluidic channel supported by a glass slide was developed (referred to herein as a "differential fluid flow chip"). The design for the device was created in AutoCAD 2015 and uploaded to the UCP Software for cutting the device. The poly-(methyl methacrylate) (PMMA) (McMaster-Carr, Atlanta, GA and ePlastics, San Diego, CA 1.5 mm and 3 mm thick) and the double sided adhesive (DSA) (3M, St. Paul, MN, 76 μm thick) were cut using a VLS 2.30 laser cutter (VersaLaser, Scottsdale, AZ). The differential fluid flow chip consisted of 1.5 mm PMMA cut into a 28.5 mm×8 mm piece. A 4 mm diameter sperm inlet was cut into the piece 28.5 mm away from a 0.764 mm fluid flow inlet. This was then attached to a piece of DSA which had a 4 mm diameter sperm inlet and a 22.4 mm×4 mm channel cut into it. The whole structure was then attached to a 75 mm×25 mm glass slide.

The system 10 for sorting sperm shown in FIG. 1B was made with 3 mm thick PMMA cut into 75 mm×25 mm. A sperm inlet (second inlet 70) of 4 mm diameter was cut 8 mm away from an elliptical sperm collection chamber (outlet 80) (long axis 6 mm, short axis 2.4 mm). The fluid flow inlet (first inlet 60) with a diameter of 1.98 mm was cut 13 mm away from the sperm inlet (second inlet 70). This piece of PMMA was then attached to a piece of 76 μm DSA with same dimensions of PMMA and a 13 mm×2 mm long channel from flow inlet to sperm inlet (8 mm from elliptical collection chamber to sperm inlet). Three pieces of 3 mm thick PMMA were then cut into dimensions of 10.6 mm×75 mm with a 4 mm diameter sperm inlet (second inlet 70). These three pieces were attached by 76 μm DSA and stacked on top of the sperm inlet (second inlet 70) of the bottom PMMA piece.

The system 10 for sorting sperm shown in FIG. 1B was made of a PDMS-based flexible housing 20 (having flow channel 100 connecting first inlet 60 to outlet 80). The PDMS-based sperm sorting housing 20 and microfluidic system allows pinching (compressing) the flow channel 100 by external force during the sperm collection step to avoid any mixing of sorted and unsorted sperm.

Figure 3:
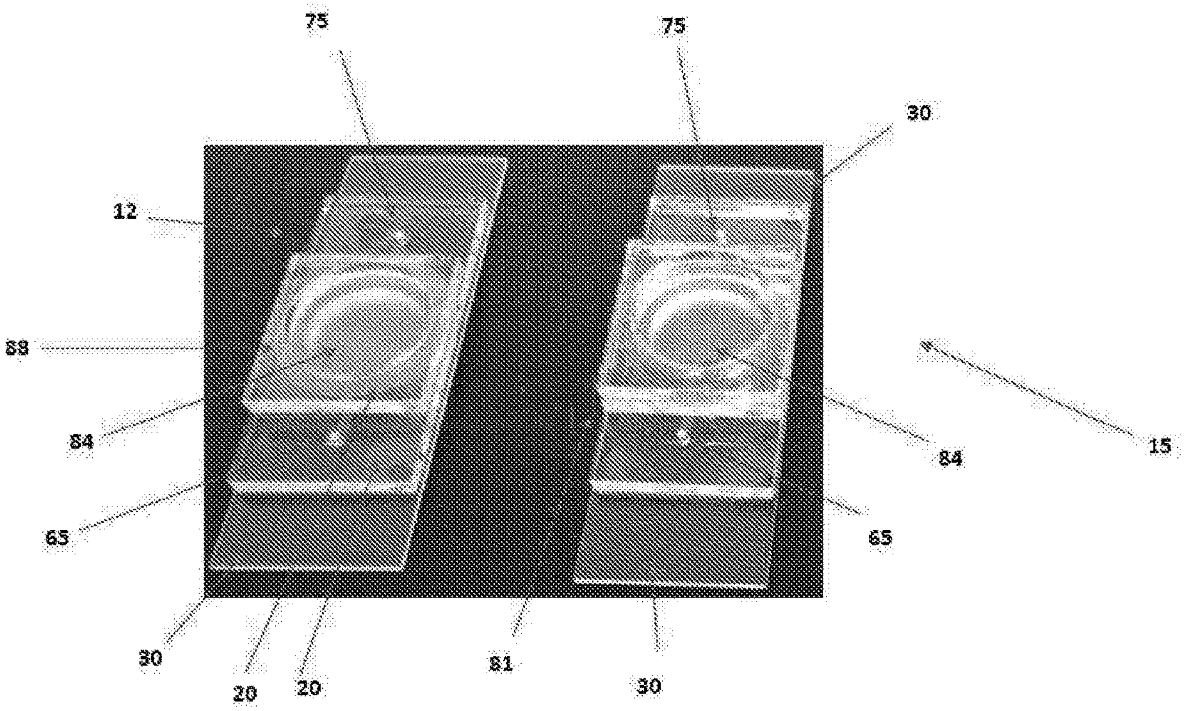
FIG. 3 is a perspective photograph of the embodiment shown in FIG. 2 (right), including a side view of a control system that is not configured for fluid flow (left). The embodiment on the right includes a microporous filter sandwiched between a top (sperm) collection chamber and a bottom chamber totaling greater than 3 mm in height that provides for a downward fluid flow, while the control system (left) includes a sperm collection chamber less than 3 mm in height and that does not provide for fluid flow.

The system 15 for sorting sperm shown in FIG. 2 and FIG. 3 consists of two inlets (at least first semen inlet 65, at least second semen inlet 75) separated by a microporous filter membrane 84. The first fluid flow 86 is initiated from top collection chamber 82 to bottom chamber 83 due to the top collection chamber height being greater than the height(s) of the at least first and second semen inlets 65, 75. In chamber 81, high quality and healthy sperm cells travel against the first fluid flow 86 upward through the microporous filter 84 into the top collection chamber 82 (FIG. 2).

Sperm Preparation

Human sperm in 1 mL vials and 0.5 mL canes were purchased from California Cryobank, Fairfax, VA and Cryos International, Orlando, FL and stored in liquid nitrogen. All semen samples were de-identified and anonymous. All methods were carried out in accordance with relevant guidelines and regulations by Institutional Biosafety Committee. Sperm was thawed at 37° C. water bath for 15 minutes before use.

Sperm Response to Flow

HTF-HEPES (InVitroCare, Frederick, MD) buffer supplemented with 1% BSA (FisherSci, Fair Lawn, NJ) was filled into a 10 mL syringe (Becton, Dickson and Company, Franklin Lake, NJ). A 17 gauge blunt needle (SAI, Lake Villa, IL) attached to 0.90" OD tubing (Cole-Parmer, Vernon Hills, IL) was attached to the syringe. The syringe was then placed on the syringe pump (New Era Pump Systems, East Farmingdale, NY) and pumped in fluid until the channel (flow channel 100) was filled with HTF-HEPES buffer. The pump was then stopped and allowed to reach an equilibrium state where no flow occurred. A 4 μL sample of semen was then loaded into the sperm inlet (second inlet 70) of the system (10) for sorting sperm shown in FIG. 1B. The sperm were allowed to swim with no flow for a period of 10 minutes to allow an ample amount of sperm into the channel (flow channel 100). At that point, the syringe pump was turned on at a flow rate of 2 μL/min, 4 L/min, 5 μL/min, 6 μL/min, 8 μL/min and 10 μL/min. The amount of sperm that oriented and swam against the flow was recorded and manually counted. The sperm motion videos were recorded using a microscope camera at 30 frames per sec (fps) before and after flow conditions. Sperm tracks were analyzed using ImageJ CASA plugin. Rheotaxis was defined as sperm head angle within ±22.5° of flow direction or the horizontal image axis.

A constant rate of 3 μL/min was used to sort sperm in the system 10 for sorting sperm shown in FIG. 1B. The collection chamber (outlet 80) was filled with 1% HTF–BSA and then covered with DSA. The syringe pump was turned on to fill the microfluidic system was with 1% HTF–BSA. A 10 μL stock sample of semen was loaded into the 4 mm diameter by 15 mm high sperm inlet (second inlet 70) of the system 10 for sorting sperm shown in FIG. 1B. The control group used a similar microfluidic system under the same conditions minus the flow. The microfluidic systems were then left to incubate for an hour before collecting sperm from the collection chamber (within outlet 80).

Sperm Concentration

Sperm from the stock, control, and flow experimental groups were counted using Makler chamber (Sefi Medical, Israel) as per the instructions and labeled as motile, non-progressively motile, or immotile. Each count was taken at least twice and the average of that count used as data point.

Sperm Velocity Analysis

The system 10 for sorting sperm shown in FIG. 1B was placed on a light microscope stage and recorded using IC Capture software (The Imaging Source, Charlotte, NC) at a location 5 mm away from the sperm inlet before and after flow for one minute at 30 (fps).

The sperm collected from the system 10 for sorting sperm shown in FIG. 1B was prepared as per WHO guidelines ("World Health Organization Laboratory Manual for the Examination and Processing of Human Semen," Geneva, Switzerland: World Health Organization, 2010). A 11 μL of sample was placed on a glass slide and covered with a 24 mm×24 mm glass cover slip to give a depth of approximately 20 μL. The sperm swimming tracks were recorded using a Nikon DS-Fi3 camera with NIS-Elements software (Nikon) attached to a light microscope for one minute at 25 fps. The videos were then uploaded to ImageJ (National Institute of Health) and analyzed using the CASA plugin to obtain the VCL, VAP and the VSL as previously demonstrated.

Statistical Analysis

Statistical analysis was performed using one-way analysis of variance (ANOVA) for all three groups, and a two-tailed t-test assuming unequal variance was used for between two groups. A p-value of less than 0.05 was considered statistically significant.

Example 3—Results and Discussion

Sperm rheotaxis is believed to be the possible long-range sperm guidance mechanism in natural sperm selection (Zhang et al., Scientific Reports 6(2016); Ishikawa et al., Biology of Reproduction 94(89), p. 81-89 (2016); Mathijssen et al., Physical Reviews Letters 116, 028104 (2016)). As described herein, microfluidic systems and devices were developed to quantitatively investigate the effect of fluid flow on human sperm guidance and selection. The flow rate of human oviductal fluid is not known, therefore, sperm rheotaxis was analyzed at various flow rates to determine the optimal shear flow where the maximum number of sperm cells show rheotaxis. From sperm rheotaxis experiments, the best flow rate determined by using the differential fluid flow chip was observed to be less than 6 μL/min.

The paths of the sperm before fluid flow follow a relatively straight curvilinear path (FIG. 5E). After flow, the sperm that were already swimming upstream continued to do so. Sperm cells whose heads were facing downstream from flow direction made an arc like trajectory to turn themselves to face into the flow (FIG. 5F). This shows the sperm are responding to the flow near a surface with a chiral flagellar pattern. The sperm tail is in a spot of higher shear flow than the head is at a surface, thus, the hydrodynamic forces and steric repulsion help turn the sperm to face upstream. In parabolic flow conditions as in the case of microfluidic channel where there is maximum flow towards the middle of the channel and almost zero flow at the boundary, the sperm long tail is subjected to more force in a high flow gradient compared to a sperm head pointing towards the wall boundary where there is minimal force due to flow. These differential forces on sperm tail and head result in the tail being dragged downstream with the head pointed upstream. As the fluid flow rate is increased above 6 μL/min, the majority of the sperm were being swept away. There was no significant difference between the sperm kinematics before and after flow when sperm cells were tracked while keeping the flow on (FIG. 5D). This is most likely due to the sperm being able to actively swim against the flow, but the flow impeding some forward progress.

It was observed that the control (no-flow) and flow groups have similar total concentrations of sorted sperm (PM+NP), but the flow group had a higher concentration of progressively motile sperm (FIG. 6A). This can be explained because the flow would select for more progressively motile and healthier sperm than a no-flow condition, which would allow for sperm with erratic swimming patterns to still traverse the channel. Both the control and flow groups contained some non-progressively motile sperm. It was observed that the PDMS-based flexible flow channels improved motility of sorted sperm significantly (99.5% motility).

The sperm that were analyzed after collection were limited to a 20 μm deep chamber that effectively kept them in the xy-plane. The flow group had velocities significantly higher than stock group (FIG. 6D). An increase in velocity is expected because only fast sperm will be able to travel the length of the channel against the stream. The increase of velocity in the control group (VCL only) over the stock group is also expected because sperm that travel down microfluidic channels have higher velocities than the stock semen sample. From these results it is clear that rheotaxis aids in selecting high quality sperm with higher velocity parameters. Mostly highly motile sperm cells are able to progress forward against the flow and small-headed immature sperm cells with broken mid pieces are not able to swim against the flow.

Other Embodiments

Any improvement may be made in part or all of the system features and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A system for sorting sperm comprising:

a housing operably connected to a substrate, the substrate having a first end and a second end;

a microfluidic system supported by the housing;

a first semen inlet positioned proximate to the first end and providing access to the microfluidic system to deliver semen to the microfluidic system, the first semen inlet having a height less than 3 mm and a diameter of from 0.1 mm to 1.0 mm and being configured to also function as a first fluid outlet during use of the system;

a second semen inlet disposed proximate to the second end and providing access to the microfluidic system to deliver semen to the microfluidic system, the second semen inlet having a height less than 3 mm and a diameter of from 0.1 mm to 1.0 mm and being configured to also function as a second fluid outlet during use of the system;

a chamber providing access to the microfluidic system, the chamber disposed between the first semen inlet and the second semen inlet for collecting sorted motile sperm from the microfluidic system, the chamber comprising a microporous filter defining a top collection chamber portion and a bottom collection chamber portion, wherein the top collection chamber portion has a height greater than a height of the bottom collection chamber portion;

the top collection chamber portion having a height that is greater than 3.5 mm and a diameter of from 15 mm to 30 mm, the bottom collection chamber portion having a height of 3 mm or less and a diameter of from 15 mm to 20 mm that is fluidly connected to the top collection chamber portion, wherein the greater height of the top collection chamber portion relative to the bottom collection chamber portion between the first and second semen inlets provides for a first fluid flow from the top collection chamber portion downward to the bottom collection chamber portion during use of the system; and a flow channel extending from the first semen inlet to the second semen inlet for sperm to enter the bottom collection chamber portion and travel upward from the bottom collection chamber portion into the top collection chamber portion, wherein the first semen inlet, the second semen inlet, and the chamber are fluidly connected to the flow channel, and wherein the flow channel between the first semen inlet and the chamber and between the second semen inlet and the chamber is from 1 mm to 10 mm in length, from 1 mm to 3 mm in width, and from 100 μm to 500 μm in height.

2. The system of claim 1, wherein the bottom chamber is 15 mm to 30 mm in diameter and greater than 6 mm in height.

3. The system of claim 1, wherein the substrate is a glass slide.

4. The system of claim 1, wherein the housing comprises a plastic.

5. The system of claim 4, wherein the plastic is Polydimethylsiloxane (PDMS), poly-(methyl methacrylate) (PMMA), or a combination thereof.

6. The system of claim 1, wherein the chamber is substantially cylindrical.

7. The system of claim 1, wherein there is a minimum of three semen inlets.

8. The system of claim 1, further comprising at least one of: a pipette and tubing operably and fluidly connected to at least one of the at least first and second semen inlets for delivering semen.

9. The system of claim 1, further comprising semen and a fluid comprising a sperm preparation buffer.

10. The system of claim 1, further comprising a heating system to maintain a temperature of 37° C.

11. The system of claim 1, wherein the microporous filter comprises a plurality of micropores sized to permit a head of a sperm to pass therethrough.

12. A system for sorting sperm comprising:

a housing operably connected to a substrate, the substrate having a first end and a second end;

a microfluidic system supported by the housing;

a first semen inlet positioned proximate to the first end and providing access to the microfluidic system to deliver semen to the microfluidic system, the first semen inlet being configured to also function as a first fluid outlet during use of the system;

a second semen inlet disposed proximate to the second end and providing access to the microfluidic system to deliver semen to the microfluidic system, the second semen inlet being configured to also function as a second fluid outlet during use of the system;

a chamber providing access to the microfluidic system, the chamber disposed between the first semen inlet and the second semen inlet for collecting sorted motile sperm from the microfluidic system, the chamber comprising a microporous filter defining a top collection chamber portion and a bottom collection chamber portion, wherein the top collection chamber portion has a height greater than a height of the bottom collection chamber portion, wherein the greater height of the top collection chamber portion relative to the bottom collection chamber portion between the first and second semen inlets provides for a first fluid flow from the top collection chamber portion downward to the bottom collection chamber portion during use of the system; and a flow channel extending from the first semen inlet to the second semen inlet for sperm to enter the bottom collection chamber portion and travel upward from the bottom collection chamber portion into the top collection chamber portion, wherein the first semen inlet, the second semen inlet, and the chamber are fluidly connected to the flow channel.

13. A method for sorting sperm comprising:

providing the system for sorting sperm according to claim 1;

delivering a sample of semen or sperm to at least one of the at least first and second semen inlets;

delivering a sufficient amount of fluid to the top collection chamber such that the top collection chamber is filled with the fluid resulting in a first fluid flow from the top collection chamber downward to the bottom chamber such that motile sperm travel against the first fluid flow upward from the bottom chamber through the microporous filter to the top collection chamber; and harvesting motile sperm that have passed through the microporous filter and entered the top collection chamber.

14. The method of claim 13, wherein harvesting motile sperm that have passed through the microporous filter and entered the top collection chamber comprises collecting the motile sperm with a pipette.

15. The method of claim 13, wherein delivering a sufficient amount of fluid to the top collection chamber comprises delivering the fluid from a syringe, tube, pipette or combination thereof.

16. The method of claim 13, wherein a second fluid flow comprising waste fluid travels away from the bottom chamber and towards the at least first semen inlet and the at least second semen inlet.

17. The method of claim 16, further comprising removing waste fluid from the at least first and second fluid outlets at one or more time points or continuously after delivering the sample of semen or sperm.

18. The method of claim 13, further comprising heating the system for sorting sperm to maintain a temperature of 37° C.

* * * * *